United States Patent [19]

Levinson et al.

[11] 4,007,273
[45] Feb. 8, 1977

[54] TREATMENT AND PRE-TREATMENT OF DYSMETRIC DYSLEXIA BY IMPROVING SEQUENTIAL SCANNING AND OCULAR FIXATION ABILITIES AND THERAPEUTIC COMPOUNDS

[76] Inventors: Harold N. Levinson, 15 Lake Road, Great Neck, N.Y. 11020; Jan Frank, 45 E 82nd St., New York, N.Y. 10028

[22] Filed: Dec. 8, 1975

[21] Appl. No.: 638,336

Related U.S. Application Data

[60] Continuation-in-part of Ser. No. 424,104, Dec. 12, 1973, abandoned, Division of Ser. No. 528,139, Nov. 29, 1974, Pat. No. 3,940,485.

[52] U.S. Cl. .............................. 424/247; 424/253; 424/267; 424/330
[51] Int. Cl.² ................. A61K 31/52; A61K 31/54; A61K 31/135; A61K 31/445
[58] Field of Search ........... 401/580; 424/263, 267, 424/247, 253, 330; 528/139

[56] References Cited

OTHER PUBLICATIONS

Modell, Drugs in Current Use & New Drugs – 1973, pp. 18, 34 & 74.

*Primary Examiner*—Stanley J. Friedman
*Attorney, Agent, or Firm*—Bauer, Amer & King

[57] ABSTRACT

The within method contemplates the administration of a drug, effective as a cerebellar-vestibular harmonizing agent, as a prelude to reading for a patient who is or will become dysmetric dyslexic, the administered drug functioning in a sense like "eyeglasses" to improve the dynamic vision of the patient.

In a partially analogous situation, in a person who suffers from motion sickness, commonly known as seasickness, the rocking of the boat or like motion produces an increased or excessive input to his cerebellar-vestibular circuits, with the result that such excessive stimulation causes nauseousness and related adverse effects. In a dysmetric dyslexic-identified patient, while he never experiences symptoms of motion sickness, i.e. nauseousness, during reading, he nevertheless has an overloading and dysharmony (i.e. excessive input) to his cerebellar-vestibular circuits as a result, obviously not of boat rocking or the like, but as a result of a dysfunctioning cerebellar-vestibular, a dysfunctioning discovered to exist in dysmetric dyslexic patients. The administered drug, of the nature indicated, thus by its suppressing and harmonizing influence maintains the input to and within the patient's cerebellar-vestibular circuits at a diminished level which significantly enhances the patient's eye tracking, and thus reading, ability.

5 Claims, No Drawings

TREATMENT AND PRE-TREATMENT OF DYSMETRIC DYSLEXIA BY IMPROVING SEQUENTIAL SCANNING AND OCULAR FIXATION ABILITIES AND THERAPEUTIC COMPOUNDS

This application is a continuation-in-part application of application Ser. No. 424,104 filed Dec. 12, 1973 now abandoned, and is a division of application Ser. No. 528,139 filed Nov. 29, 1974 now U.S. Pat. No. 3,940,485.

Applicants hereby disclaim and dedicate to the public the terminal part of the term of any patent or patents granted on the within application still in effect on or after the end of the term of any patent or patents granted on said application Ser. No. 528,139.

The present invention relates to a method of preparing a patient previously identified as being dyslexic because of dysfunctioning cerebellar-vestibular circuits, for reading activity.

Underlying the preparation method of the present invention is the discovery that the condition of dysmetric dyslexia is attributable to a cerebellar-vestibular dysfunction. This is contrary to the more widely accepted belief in the medical profession that the condition of organically determined dysmetric dyslexia is due solely or at least primarily to a dysfunction of the cortex. It suffices, however, for the present purposes to indicate that the aforesaid cerebellar-vestibular dysfunction manifested in dysmetric dyslexic children is proved by positive Rombergs, difficulty in tandem walking, articulatory speech disorders, dysdiadochokinesis, hypotonia, and various dysmetric or past pointing disturbances during finger-to-nose, heel-to-toe, writing, drawing, as well as during ocular fixation and scanning testing.

Another significant medical discovery underlying the present invention is that there exists in dysmetric dyslexic children a sub-clinical nystagmus or eye vibration at an almost imperceptible frequency or number of beats per second. Here also, for present purposes, it suffices to indicate that the existence of this sub-clinical nystagmus or eye vibration is demonstrated by electronystagmographic recordings when the eyes were closed to eliminate fixation, as this tends to inhibit nystagmus.

With children suffering from the condition indicated, there is at all times movement in their eyes occurring at approximately one beat per second, which interferes with the vision of these children. This abnormal eye movement is, as noted, sub-clinical in nature, in that measurement thereof requires an electronystagmographic frequency recording under favorable conditions.

The foregoing sub-clinical dysfunction or nystagmus has, in turn, been traced to the presence of a cerebellar-vestibular dysfunction which prevents ocular fixation and sequential scanning of letters and words in a proper manner. Specifically, during sequential scanning or normal reading by dysmetric dyslexic children, letters and words are disordered, and letter and word scrambling or blurring results. For example, the biggest or first letter of the word is often fixated first during the slow right-to-left phase of the nystagmus. The rapid left-to-right phase often skips over several letters or a whole word until another letter is automatically fixated and scrambling or blurring results. The patient, therefore, confuses letters and words which differ only or mainly in spacial placement, i.e. b=d=p=q, a=e, e=3, c=u, m=w, saw=was, no=on, et cetera. The aforesaid confusion of letters and words results in reading difficulties, as indicated below.

Specifically, a Position Paper on READING DISABILITIES IN YOUR CHILD of the American Association of Ophthalmology presented and distributed at the Forum, "THE RIGHT TO READ" of the White House Conference on Children, Washington, D. C., Dec. 14, 1970, entitled, "DYSLEXIA" defines the term "dyslexia" as a difficulty in reading or reading disability because of a poor understanding of printed words. Dyslexia caused by obvious conditions such as prolonged absence from school, psychological problems, or obvious (generally cortical) brain defects is identified as "secondary dyslexia". The dyslexia which is stated to be of unknown origin is referred to as "specific primary dyslexia or developmental dyslexia". The paper continues with the teaching that eye defects do not cause specific primary dyslexia because the dyslexia is based on recognition and not on vision. This view is representative of the widely accepted belief of the medical profession that this form of dyslexia is caused by an inability of the brain to recognize what the eye sees (see, for example: "Reading Disability" edited by John Money, pp. 9–16 and 45–60, The Johns Hopkins Press (1962); and Vol. 20, No. 3, August 1973 issue of "Pediatric Clinics of North America", pp. 587–597 and 599–605). Primary dyslexia was therefore attributed to a dysfunction of the cortex.

Since dyslexia was defined as a reading disability, children suffering from dyslexia were not found until they were discovered to be deficient readers. In many cases, the child is about two years behind its age group in reading by the time the reading difficulties are attributed to primary dyslexia rather than other causes. In most cases, the symptoms of this form of dyslexia tend to disappear when the child reaches about ten to twelve years of age, depending upon the child's rate of maturation. When the symptoms of primary dyslexia are no longer apparent, the child's ability to learn to read approaches normal. However, the child is often about two years behind its age group with consequent emotional and behavior problems.

An important contribution of the present invention is therefore, firstly, the recognition that the aforesaid discovered conditions existing in a dysmetric dyslexic patient contribute to his poor response to reading instruction, and secondly, devising the within method according to which said patient can be properly prepared for reading so as to significantly improve his reading performance. For a better understanding of this contribution, it is worthwhile to make reference to a partially analogous situation. Specifically, in a person who suffers from motion sickness, commonly known as seasickness, the rocking of the boat or the like produces an increased or excessive input to his cerebellar-vestibular circuits and overloading thereof. As a result of this excessive stimulation and overloading, the person experiences nausea and other such symptoms, the same having an adverse effect on the autonomic nervous system which regulates and monitors the gastrointestinal tract and related centers.

In connection with motion sickness, use is therefore made of certain drugs which have the effect of harmonizing, suppressing or causing a diminution of the input to and within the cerebellar-vestibular circuits. How these drugs achieve this result is not exactly known.

In connection with a dysmetric dyslexic person, although this person never experiences nauseousness or other symptoms of motion sickness during reading, an important part of the present invention is the recognition that such a person, nevertheless, has an overloading or dysharmony of his cerebellar-vestibular as a result, obviously not of boat rocking or the like, but as the result of the dysfunction of the circuits thereof. It is during reading that the patient is called upon to exhibit ocular fixation and sequential scanning (tracking) of dynamic vision. Thus, whereas a dysmetric dyslexic person will perform as well as a normal person on eye tests measuring "static" vision or visual acuity — identification of stationary objects of fixed height at a specific distance, when said dysmetric dyslexic person is required to follow a moving target, i.e. track, the eye vibration or nystagmus and dysmetric ocular pursuit, which are the conditions discovered to exist in such a person, results in ocular overshooting and undershooting, and in turn, results in failure to focus and sequentially track the material being read.

As a result of the above dysfunction of the cerebellar-vestibular circuits, there is a failure to harmonize, regulate and control the cerebellar-vestibular input and this leads to an overloading of the cerebellar-vestibular circuits. The practice of the within method of preparing a dysmetric dyslexic person for reading thus contemplates the administration of drugs selected from those which have in the past been used as a treatment for motion sickness. This person, after taking the prescribed drug, is better able to track and therefore, better able to see objects in motion or, what amounts to the same thing, is better able to see stationary objects or reading material while his head and eyes are in motion, as during reading or scanning. In either case, there is relative motion which ordinarily adds to the eye vibration resulting from the dysfunctioning of the cerebellar-vestibular circuits that prevents proper fixation by the person, but which is diminished by the taking of the drug and, as a result, permits the person to better fix on the object and thus track it. In effect, therefore, a drug used as hereinafter prescribed, functions in a sense like "eyeglasses" to improve the dynamic vision of the person or dysmetric dyslexic patient. Such patient may be identified by the well known Barany's caloric stimulation of the vestibular apparatus, by utilizing electrostagmographic recordings, or by using the screening procedure of U.S. Pat. No. 3,842,822, issued on Oct. 22, 1974. Following identification, by any of the foregoing, and as preparation for improved reading and scanning performance according to the present invention, the patient for a selected period of time prior to scanning or reading is to have administered the below prescribed drugs, said period of time being that which is adequate to allow the administered drug or drugs to have its beneficial effect on the patient.

THE PRESCRIBED DRUGS

The presently preferred cerebellar-vestibular harmonizing drugs are cyclizine, diphenhydramine, dimenhydrinate, diphenidol, cinnarizine, meclizine, buclizine, and promethazine. The daily dosage which may be continued over a period of months and even years varies with the characteristics of the child. For convenience, the dosage rate is broken down into the treatment of the age group three–six and seven–twelve. The older children can generally tolerate larger amounts of the drug. Since the preferred cerebellar-vestibular harmonizing drugs include antihistamines, which are known to have a tendency to induce drowsiness, the maximum amount which the child will tolerate is the amount at which the child does not become drowsy. The drug is preferably administered three times daily to minimize the tendency toward drowsiness.

The dosage of dimenhydrinate and diphenidol is between about 25 and 100 mg, and preferably between about 50 and 100 mg. The daily treatment is preferably about 25 mg three times daily. For the seven–twelve age group, the treatment is between about 40 and 100 mg daily and preferably between about 75 and 100 mg daily. The preferred daily dosage is about 35 mg three times daly or 50 mg twice daily.

The dosage using diphenhydramine with the age group three–six is between 9 and 40 mg per day and preferably between 20 and 30 mg per day. The preferred treatment is 10 mg three times daily. With the seven–twelve age group, the daily dosage is from about 20 to 75 mg and preferably from about 50 to 75 mg, with treatments of 25 mg three times daily preferred.

With promethazine, the daily treatment for the three–six age group is from 6 to 25 mg with between 6 and 15 mg preferred. The daily treatment is preferably 2 or 3 mg three times daily. With the seven–twelve age group, the daily total is from about 12 to 30 mg with 15 to 25 mg being preferred. The preferred treatment for the seven–twelve age group is about 5 mg three times daily.

The specific active compounds disclosed herein are usually administered in the form of one of their pharmaceutically acceptable acid salts, such as the hydrochloride, the sulfate or the phosphate. The drugs may be administered orally or even by injection (subcutaneous or intermuscular) by suppository, by inhaling, e.g. a nasal spray, or even by skin absorption.

The dosage of diphenhydramine used in the treatment of children (starting at the noted age) is disclosed in the following table. The treatment varied from about one month to eight months.

| AGE | DIPHENHYDRAMINE | |
|---|---|---|
| Year – Month | mg Unit Dose | Unit Dose Daily |
| 7 – 6 | 25 | 3x |
| 8 – 2 | 25 | 3x |
| 7 – 8 | 25 | 3x |
| 7 – 9 | 50 | 2x |
| 6 – 11 | 25 | 3x |
| 14 – 4 | 50 | 2x |
| 10 – 10 | 50 | 2x |
| 11 – 5 | 50 | 2x |
| 10 – 0 | 50 | 2x |
| 7 – 9 | 2.5 | 3x |
| 9 – 6 | 2.5 | 3x |
| 7 – 7 | 2.5 | 3x |
| 7 – 9 | 2.5 | 3x |
| 7 – 4 | 12.5 | 3x |
| 7 – 10 | 25 | 3x |
| 7 – 6 | 50 | 2x |
| 8 – 3 | 25 | 3x |
| 7 – 10 | 21.5 | 3x |
| 8 – 3 | 25 | 3x |
| 7 – 0 | 25 | 3x |

All of the children treated were selected because they exhibited symptoms of dysmetric dyslexia. They had been tested for sequential scanning and ocular fixation and both tests established that these children had substandard sequential scanning and ocular fixation.

As a consequence of the treatment or preparation method described herein, children exhibiting dysmetric dyslexia have improved ocular fixation and sequential scanning and when reading during the effective period of the administered drug exhibit a significant improvement in their reading ability.

A latitude of modification, change and substitution is intended in the foregoing disclosure and in some instances some features of the invention will be employed without a corresponding use of other features. Accordingly, it is appropriate that the appended claims be construed broadly and in a manner consistent with the spirit and scope of the invention herein.

What is claimed is:

1. A method of obviating eye tracking difficulties for a dysmetric dyslexic patient preparatory to said patient participating in reading or scanning activity, which method is based on the discoveries of a cerebellar-vestibular dysfunction and a resulting sub-clinical eye oscillation indicative of said dysfunction, said method comprising the steps of preceding any reading or scanning by such patient with an administered quantity of a cerebellar-vestibular harmonizing drug selected from the group consisting of diphenhydramine, dimenhydrinate, diphenidol and promethazine in a dosage effective to suppress input to and within said patient's cerebellar-vestibular circuits, and only allowing reading or scanning activity by said patient during the effective period of said administered drug, whereby the adverse effect of said sub-clinical eye oscillation as input to said patient's cerebellar-vestibular circuits is obviated by said drug during said reading or scanning activity to thereby enhance said patient's eye tracking ability.

2. The method of claim 1 wherein said cerebellar-vestibular harmonizing drug is diphenhydramine.

3. The method of claim 1 wherein said cerebellar-vestibular harmonizing drug is dimenhydrinate.

4. The method of claim 1 wherein said cerebellar-vestibular harmonizing drug is diphenidol.

5. The method of claim 1 wherein said cerebellar-vestibular harmonizing drug is promethazine.

* * * * *